United States Patent [19]

Yagi et al.

[11] Patent Number: 5,281,314

[45] Date of Patent: Jan. 25, 1994

[54] METHOD OF MEASURING HUMIDITY BY USING AN ELECTROCHEMICAL CELL

[75] Inventors: Hideaki Yagi; Katsuhiko Horii, both of Nagoya, Japan

[73] Assignee: NGK Spark Plug Co., Ltd., Nagoya, Japan

[21] Appl. No.: 716,914

[22] Filed: Jun. 18, 1991

[30] Foreign Application Priority Data

Jun. 19, 1990 [JP] Japan .................................. 2-160742

[51] Int. Cl.$^5$ .............................................. G01N 27/26
[52] U.S. Cl. .......................... 204/153.22; 204/153.16; 204/153.18; 204/153.1; 204/426; 204/428
[58] Field of Search ...................... 204/153.22, 153.18, 204/153.16, 153.1, 426, 428

[56] References Cited

U.S. PATENT DOCUMENTS 4,851,103  7/1989  Usami et al. .................... 204/153.18
4,938,847  7/1990  Andrews, Jr. et al. ........ 204/153.22

Primary Examiner—John Niebling
Assistant Examiner—Bruce F. Bell
Attorney, Agent, or Firm—Cooper & Dunham

[57] ABSTRACT

In a method of measuring humidity of an oxygen-containing gas by using an electrochemical cell, firstly an voltage is applied across the pair of the electrodes to obtain a characteristic curve between an intensity of the voltage and that of electrical current, the characteristic curve continuously originating from a first flat portion in which a first diffusion limit current generally remains constant within a predetermined voltage range, and ending up in a second flat portion in which a second diffusion limit current generally remains constant within a predetermined voltage range. Secondly each value of the first diffusion limit current and the second diffusion limit current is read out, and an arithmetic ratio of the first diffusion limit current to the second diffusion limit current is calculated to obtain the humidity of the gas.

1 Claim, 8 Drawing Sheets

METHOD OF MEASURING HUMIDITY BY USING AN ELECTROCHEMICAL CELL

BACKGROUND OF THE INVENTION

1. Field of the Invention

This invention relates to a method of measuring humidity of an oxygen-containing gas by using an electrochemical cell of an oxygen-ion conductive electrolyte on which a pair of electrodes are placed.

2. Description of the Prior Art

In a humidity measurement device using the electrochemical cell, there have been devices known in Japanese Patent Provisional Publication Nos. 60-222761, 62-150151 and 62-150152.

In the Japanese Patent Provisional Publication No. 60-222761, partial pressure of an oxygen component in moisture-laden gas is measured with the function of limit currents, each value of which is obtained before and after removing aqueous vapor component from the gas.

The Japanese Patent Provisional Publication No. 62-150151 teaches that the limit currents due to gas diffusion are obtained depending on an oxygen density and an aqueous density in the gas. The difference between values of the limit currents leads to humidity measurement.

Further, the Japanese Provisional Publication Pat. No. 62-150152 suggests that a first limit current due to an oxygen density and a second limit current due to an aqueous density are obtained. Then, a third limit current based on a moisture-laden gas is obtained. The humidity is measured based on the difference between the third limit current and, at least, one of the first and second limit currents.

In each device according to the Japanese Patent Provisional Publication Nos. 60-222761, 62-150151 and 62-150152, however, a drying device is required to desiccate the gas to remove aqueous vapor. It is, simultaneously, necessary for the prior devices to measure the limit current. Thus necessitates a large scale measurement system as a whole, and at the same time, resulting in a slow response to operation of the humidity measurement.

On the other hand, porous electrodes or porous oxygen-ion diffusion limiting means is provided in the solid electrolyte, variation of the porosity inevitably occurs according to individual products. The same is true with thickness and density of the solid electrolyte. This causes to establish variation in diffusion limit currents due to conductivity difference of the electrolyte and various gas diffusions under a certain voltage applied across the electrodes, thus resulting in discordance with humidity of the gas. Further, replacement of parts and elements of the device becomes difficult in ensuring the humidity measurement.

Moreover, the electrolysis between the electrode and the solid electrolyte tends to deteriorate an interface therebetween with the moisture so as to gradually alter the characteristics of the electrochemical cell, thus making it impossible to ensure a stable humidity measurement for an extended period of time.

Therefore, the invention has its object to provide a method of measuring humidity, which is capable of eliminating all the drawbacks mentioned above.

It is an object of the invention to provide a method of measuring humidity which is capable of maintaining measurement of humidity level to be unchanged for an extended period of time with high accuracy.

It is an object of the invention to provide a method of quickly and easily measuring humidity.

SUMMARY OF THE INVENTION

According to the invention, there is provided a method of measuring humidity by using an electrochemical cell which includes a solid type of an oxygen-ion conductive electrolyte, a pair of porous electrodes tightly placed on a surface of the electrolyte, and one of the electrodes being arranged to be partly exposed to moisture-laden gas so that oxygen component of the gas is transferred from one electrode to the other electrode by a pumping action in accordance with an intensity of voltage applied across the pair of the electrodes: the method of measuring humidity comprising steps of: applying the voltage across the pair of the electrodes to obtain a characteristic curve between an intensity of the voltage and that of electrical current, the characteristic curve continuously originating from a first flat portion in which a first diffusion limit current generally remains constant within a first predetermined voltage range, and passing a point of an inflection with an increase of the applied voltage in which a second differential derivative of the characteristic curve falls on zero at a certain voltage, and ending up in a second flat portion in which a second diffusion limit current generally remains constant within a second predetermined voltage range; reading out a value of the first diffusion limit current within the predetermined voltage range, and reading out a value of the second diffusion limit current within the second predetermined voltage range; and calculating an arithmetic ratio between the value of the first diffusion limit current and that of the second diffusion limit current on the basis of the fact that the arithmetic ratio substantially remains uniform under a certain humidity of the moisture laden gas, regardless of deterioration of the electrochemical cell.

The invention is made on the basis of the fact that the arithmetic ratio between the first and second diffusion limit current remains substantially uniform under a certain humidity, and changes only depending on humidity of the moisture-laden gas when voltage is applied across the electrodes. In addition, this uniformity of the arithmetic ratio remains independently unchanged with the lapse of time regardless of the moisture-deterioration of the interfaces between the solid electrolyte and the electrodes in the electrochemical cell, according to our discovery.

The humidity of the moisture-laden gas is obtained as follows:

Firstly the first diffusion limit current is read when the first flat portion appears on the characteristic curve. Secondly the second diffusion limit current is read when the second flat portion appears on the characteristic curve.

The arithmetic ratio between the first and second diffusion limit current is calculated to readily determine the humidity of the moisture-laden gas, according to the invention, since the calculated ratio is in accordance with the humidity of the gas: the arithmetic ratio shows a continuous and almost linear curve as the function of aqueous vapor pressure of the gas to be measured as shown in FIG. 7.

If the arithmetic ratio curve is treated in advance by a linearized circuit and an amplifier or by a microcomputer, etc., reading of the ratio is the instant and accurate value of the humidity of the gas to be measured.

The arithmetic ratio is a valid measure of humidity regardless of deterioration and dimensional variation which the electrochemical cell undergoes, and thus enables measurement of the humidity for an extended period of time with high accuracy.

Calculating the arithmetic ratio obviates the necessity of drying the moisture laden gas and ensures the humidity measurement in good response with a relatively simple construction.

These and other objects and advantages of the invention will be apparent upon reference to the following specification, attendant claims, and drawings.

DETAILED DESCRIPTION OF THE INVENTION

Figure 1:
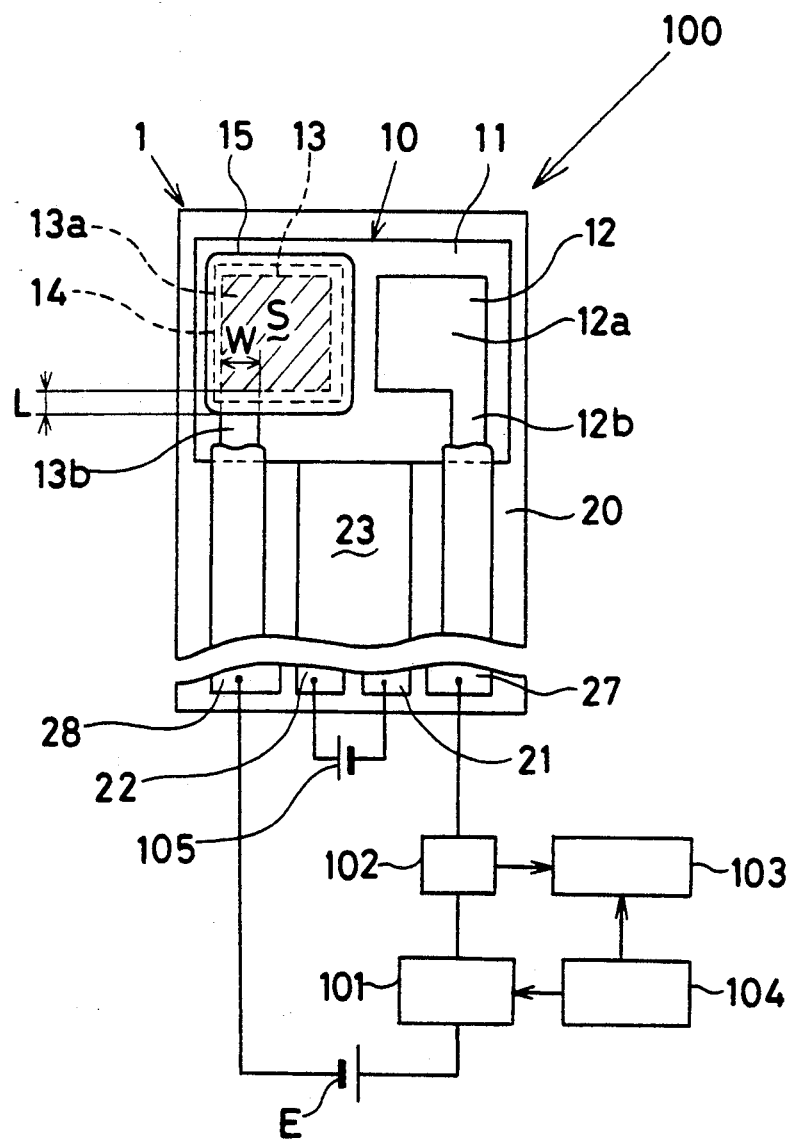
FIG. 1 is a plan view of an electrochemical cell to serve as a humidity measurement device according to an embodiment of the invention, but partly broken away.
Figure 2:
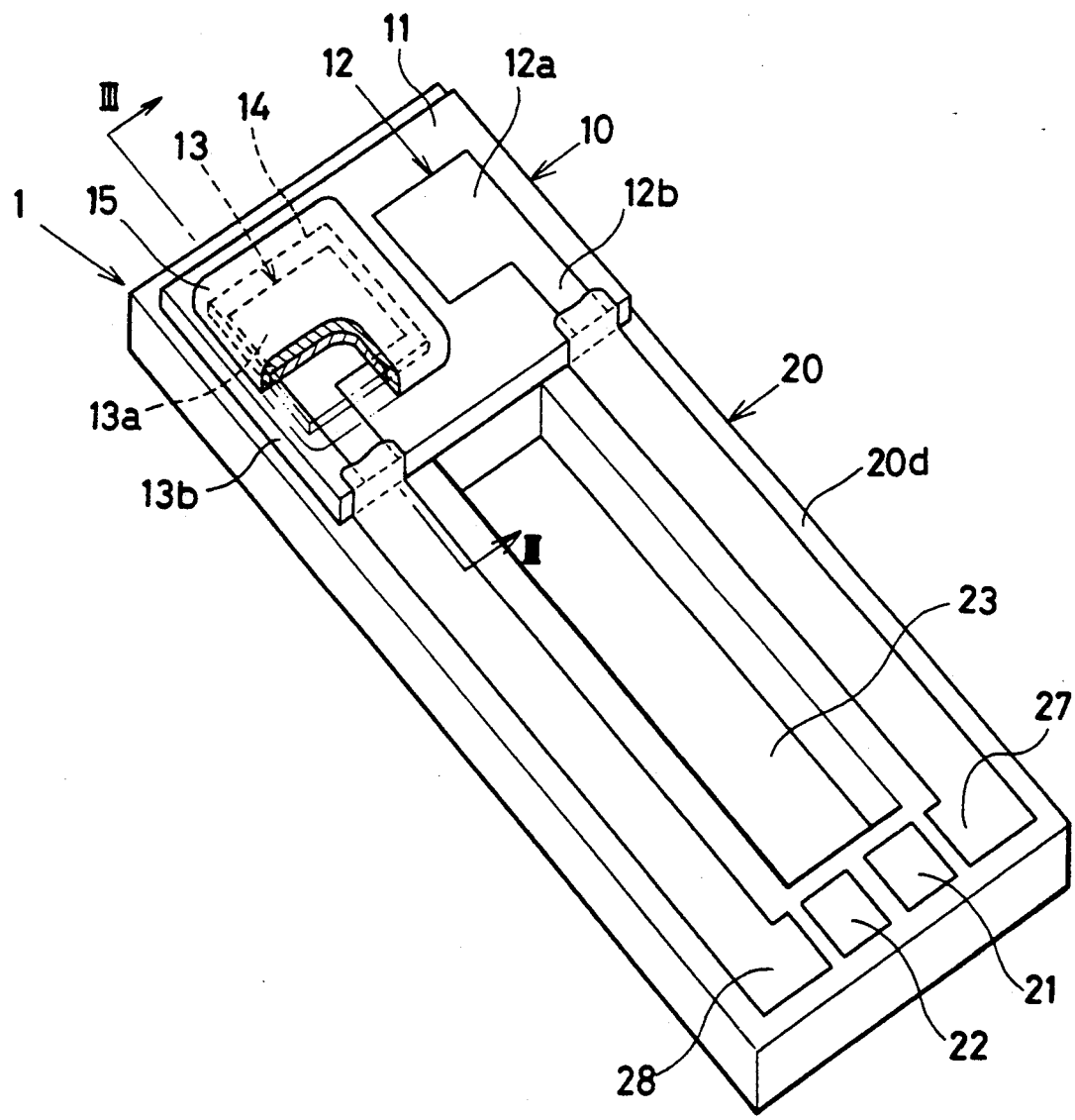
FIG. 2 is a perspective view of the electrochemical cell shown as a humidity measurement device in FIG. 1.

Referring to FIG. 1 and 2 in which an electrochemical cell 1 is shown to serve as an oxygen concentration sensor. The electrochemical cell 1 comprises a sensor element 10 and a ceramic heater 20. The sensor element 10 includes an oxygen-ion conductive plate 11, and a porous anode electrode 12, a porous cathode electrode 13, an alumina porous layer 14 and a glaze layer 15.

Figure 3:
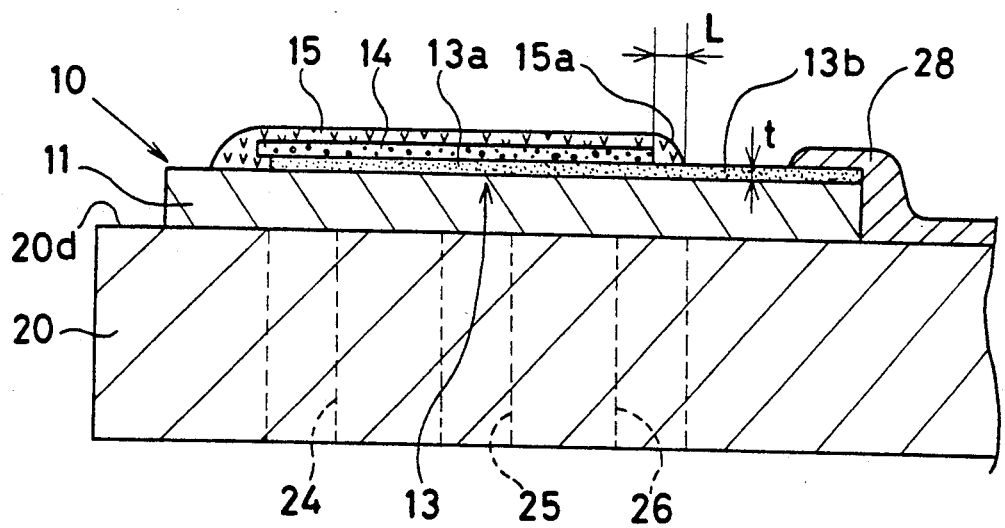
FIG. 3 is a cross-sectional view of the electrochemical cell taken along the line III—III.

The oxygen-ion conductive plate 11 is made from a solid solution of zirconia partially stabilized by yttrium oxides to serve as a solid electrolyte. The oxygen-ion conductive plate 11 is in the shape of rectangle, and measures 5 mm × 7 mm in square dimension and 0.3 mm in thickness. On an upper surface of the oxygen-ion conductive plate 11, the anode and cathode electrodes 12, 13 are located right and left at a predetermined interval which in turn has electrode portions 12a, 13a and connection portions 12b, 13b. Each of the electrodes 12, 13 is made of porous platinum sintered on the oxygen-ion conductive plate 11 at the temperature of 1500 degrees Celsius after they were printed on the plate 11. On the oxygen-ion conductive plate 11, the alumina porous layer 14 is coated in a manner to cover the electrode portion 13a, and only partly covering the connection portion 13b. The alumina porous layer 14 is covered by a glaze layer 15 together with the electrode portion 13a and the connection portion 13b to prevent moisture-laden gas from being in contact with the electrode portion 13a except for the connection portion 13b. The alumina porous layer 14 and the glaze layer 15, thus coated on the oxygen-ion conductive plate 11, are attached by baking them at the temperature of 850 ~ 900 degrees Celsius. The electrode portion 13a is isolated from the moisture-laden gas, but the connection portion 13b is exposed outside from the glaze layer 15 as shown in FIG. 3.

In this instance, the moisture-laden gas is often, referred to as a gas hereinafter in which its humidity level is to be measured according to the method of the invention.

At the connection portion 13b which is situated between a lower edge 15a of the glaze layer 15 and the oxygen-ion conductive plate 11, the connection portion 13b serves as a gas diffusion limiting aperture which works to limit an amount of oxygen gas diffusion and the moisture-laden gas diffusion so as to regulate the moisture-laden gas from entering the electrode portion 13a when voltage is applied across the electrodes 12, 13. Each of the electrodes 12, 13 measures 2.5 mm × 2.5 mm in square dimension and 20 microns in thickness (t). The connection portion 13b has a width (W) of 1 mm, and a length (L) of 2 mm covered partly by the glaze layer 15.

The amount of the gas diffusion toward the electrode portion 13a through the connection portion 13b, is in proportion to a cross sectional area (s) described hereinafter, but in inverse proportion to the length (L) of the connection portion 13b, wherein the cross sectional area (s) is given by the product of the width (W) and thickness (t) of the connection portion 13b which acts as a gas diffusion limiting aperture.

An effective ratio (R) by which the diffusion limit current can be effectively controlled is determined. Where the cross sectional area (s) of the connection portion 13b, the surface area (S) of the electrode portion 13a and the length (L) are as follows:

$$R = s/L/S = 1 \times 10^{-5} \sim 8 \times 10^{-2}.$$

According to the embodiment of this invention, the formula $R = 1.6 \times 10^{-3}$ is obtained since the relationship among (s), (L) and (S) are s=0.02, L=2, S=6.25 in turn.

Figure 4:
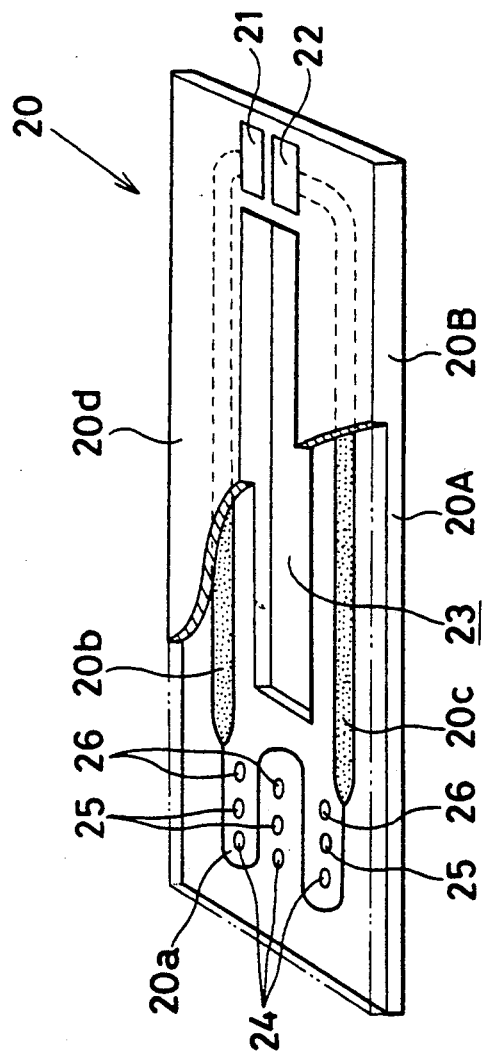
FIG. 4 is a perspective view of a ceramic heater illustrated incorporated into the electrochemical cell.

In the meanwhile, the sensor element 10 is bonded on the ceramic heater 20, with an aid of vitreous adhesive (not shown), and baked together at the temperature of approximately 800 degrees Celsius. The ceramic heater 20 is in the form of a substrate heater as shown in FIG. 4 which is manufactured by baking a green sheet 20A made of 96% alumina on which an appropriate resistor pattern 20a is previously made by printing tungsten (wolfram) paste. On the green sheet 20A, another green sheet 20B is integrally laminated by simultaneously sintering the two sheets 20A and 20B.

On the other hand, the resistor pattern 20a is connected at their respective ends to heater-electrodes 21, 22 provided on an outer surface 20d by way of conductive patterns 20b, 20c. Since the gas diffusion limiting action is effected at the connection portion 13b of the cathode electrode 13 in accordance with the invention, the resistor pattern 20a is adapted to locally heat the electrode portions 12a, 13a so as to prevent an oxygen pumping from occurring on the connection portion 13b which is so adapted to be normally kept comparatively at low temperature.

In the meanwhile, the ceramic heater 20 has a central opening 23 to effectively heat the sensor element 10, and including a plurality of rows of perforations 24, 25 and 26 are made in the area where the sensor element 10 is placed. On the surface 20d of the ceramic heater 20, there is provided sensor electrodes 27, 28 which are in turn connected to the connection portions 12b, 13b by means of ruthenium printed pattern for the purpose of energizing the electrodes 12, 13.

It is noted that the sensor electrodes 27, 28 are adapted to be printed on the surface 20d of the ceramic heater 20 at the same time when the sensor element 10 is baked on the ceramic heater 20.

The electrochemical cell 1, thus constructed, is adapted to serve as a sensing portion of the humidity measurement device 100 to measure a relationship between voltage and current when voltage is applied across the sensor electrodes 27, 28 by means of a power source (E).

The humidity measurement device 100 has a voltage controller 101, a current measurement portion 102, a calculator portion 103 and a controller unit 104. The humidity measurement device 100 is adapted to transform the power source (E) into a first voltage and a second voltage each corresponding to a first flat portion (F1) and a second flat portion (F2) depicted in a characteristic curve (A) in FIG. 5 as described in detail hereinafter. The first flat portion (F1) and the second flat portion (F2) are reduced to a first diffusion limit current (IL1) and a second diffusion limit current (IL2) also depicted in the characteristic curve (A) as described in detail hereinafter. On the basis of an arithmetic ratio (RI) between the first diffusion limit current (IL1) and the second diffusion limit current (IL2), humidity of the moisture-laden gas is to be measured.

In this instance, the ceramic heater 20 is energized by an auxiliary power source 105 to keep the electrode portions 12a, 13a at the temperature of 300~700 degrees Celsius.

With the structure thus far described, the electrochemical cell 1 is placed in the moisture laden gas which humidity is to be measured. The voltage applied across the electrodes 12, 13 causes to ionize oxygen gas in the electrode portion 13a which is covered by the glaze layer 15. As a result, the oxygen component in the moisture-laden gas which reaches through the gas diffusion aperture of the porous connecting portion 13b, is pumped from the cathode electrode 13 to the anode electrode through the sensor element 10 of oxygen-ion conductive electrolyte in accordance with the voltage applied across the electrodes 12, 13. At this time, only the electrode portion 13a is locally heated so that the oxygen component diffuses into the electrode portion 13a through the connection portion 13b which is not heated and normally kept comparatively at low temperature. The diffusion amount of oxygen component into the electrode portion 13a is limited by the gas diffusion limit aperture of the connection portion 13b in accordance with the density of the oxygen in the moisture laden gas.

Figure 5:
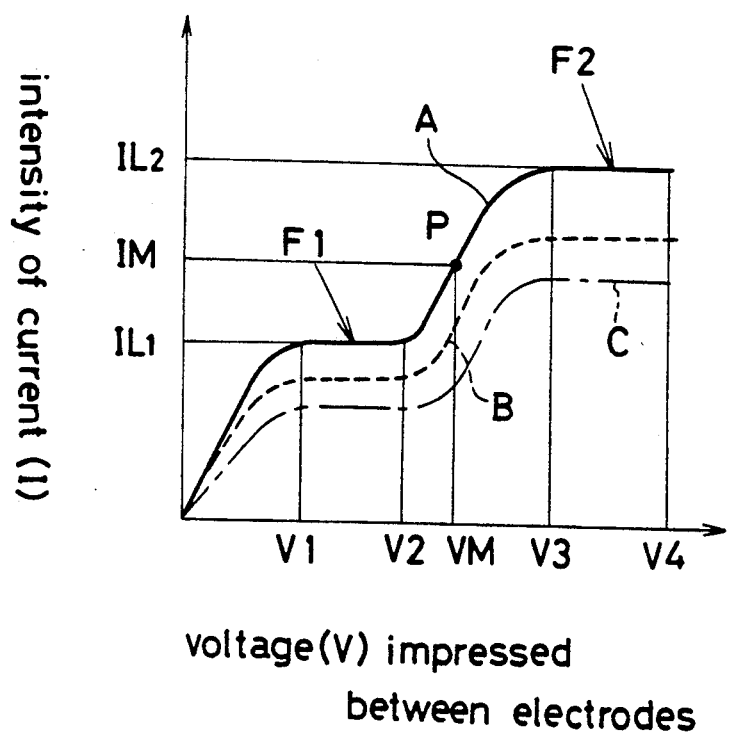
FIG. 5 is a view of characteristic curves showing the relationship between an intensity of voltage and that of current according to the electrochemical cell.

The limited amount of gas diffusion accompanies with current restriction to be represented as the first diffusion limit current (IL1) or the second diffusion limit current (IL2) as seen in the range of the first flat portion (F1) or the second flat portion (F2) in FIG. 5.

At solid line in FIG. 5, the characteristic curve (A) is depicted between an intensity of the voltage and that of the current flow across the electrodes under a certain humidity level.

The characteristic curve (A) continuously originates from the first flat portion (F1) which the first diffusion current (IL1) remains substantially constant within the first predetermined voltage range V1~V2, and passes through a point of inflection (P) at which its second differential derivative falls on zero, and ends up in the second flat portion (F2) in which the second diffusion limit current (IL2) remains substantially constant within the second predetermined voltage range V3~V4.

The first diffusion limit current (IL1) which is lower than the inflection current (IM) decreases with the increase of aqueous or rather humidity density of the gas simply because a partial pressure of the oxygen component decreases with the increase of the aqueous density in the moisture-laden gas. When the impressed voltage increases at its magnitude higher than the inflection voltage (VM), the second diffusion limit current (IL2), increases with the increase of the aqueous density of the gas, because the aqueous component ($H_2O$) in the moisture-laden gas is dissolved to produce additional oxygen-ions which are pumped together to the anode electrode 12 from the cathode electrode 13. Although the aqueous component which diffuses into the electrode portion 13a through the connection portion 13b is controlled or rather limited to thereby make the current level (IL2) flat or constant in the predetermined voltage range, the aqueous density of the moisture-laden gas increases the level of the second diffusion limit current (IL2).

Since the oxygen diffusion and aqueous diffusion are limited at the connection portion 13b of the cathode electrode 13, the second limit current (IL2) increases in proportion to the humidity, while the first limit current (IL1) increases in inverse proportion to the humidity under a constant density of oxygen component in the moisture-laden gas.

The first and second limit current (IL1), (IL2) are determined depending on the oxygen diffusion limiting means, area of the electrode portion 13a, and density and thickness of the oxygen-ion conductive plate 11. Therefore, as shown at broken lines (B) and dot-dash lines (C) in FIG. 5, different characteristic curves are represented depending on dimensional variation, etc., when individual electrochemical cells are produced.

However, it is found from indefatigable and strenuous efforts that the arithmetic ratio (i.e. RI=IL2/IL1) between the first diffusion limit current (IL1) and the second diffusion limit current (IL2) substantially remains uniform and unchanged under a certain humidity level, regardless of the deterioration or variation of the electrochemical cell with the lapse of time. Therefore the previous arrangement between the arithmetic ratio (RI) and the humidity level enables to stably measure a relative humidity level of the moisture-laden gas containing oxgen where the electrochemical cell 1 is placed, according to the invention.

The method of measuring humidity level of the moisture-laden gas is as follows:

Firstly a predetermined voltage is applied across the electrodes 12, 13 to obtain the characteristic curve (A).

Secondly the first diffusion limit current (IL1) and the second diffusion limit current (IL2) are read out respectively.

Then the arithmetic ratio (e.g. RI=IL2/IL1) between the first diffusion limit current (IL1) and the second diffusion limit current (IL2) is calculated to simply determine humidity level of the moisture-laden gas.

Figure 6:
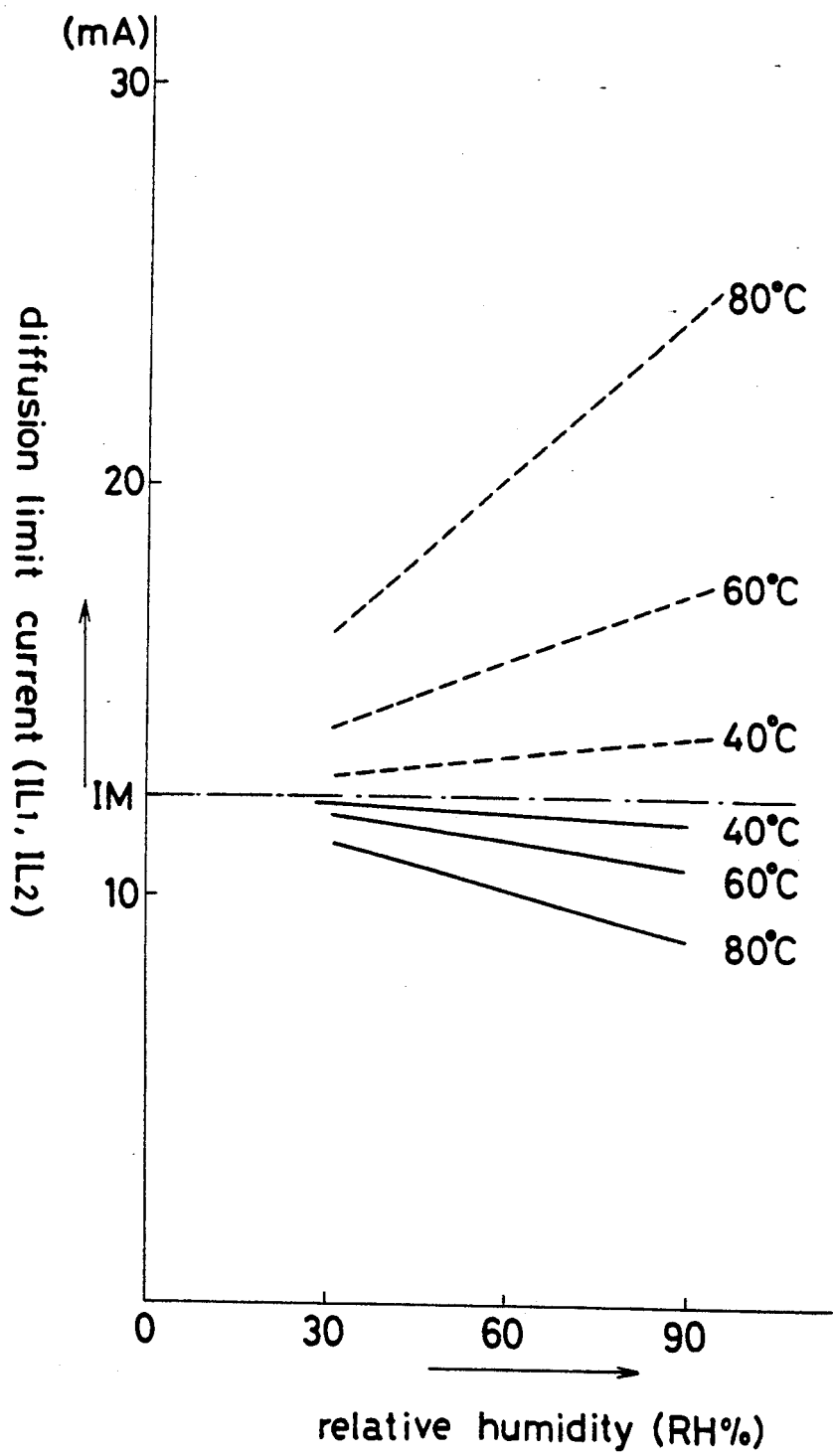
FIG. 6 is a view of characteristics showing the relationship between current and humidity according to the electrochemical cell.

FIG. 6 shows characteristics between the relative humidity level (RH %) and the diffusion limit current level under a constant density of oxygen component in the moisture-laden gas. In FIG. 6, the diffusion limit current levels (LI1) at the first flat portion (F1) are shown by solid line, while the diffusion limit current levels (LI2) at the second flat portion (F2) shown by broken lines when the temperature of the vapor-laden gas in turn changes to 40, 60 and 80 degrees Celsius. Dot-dash lines in FIG. 6 represent the current level (IM) corresponding to the point of inflection (P).

Figure 7:
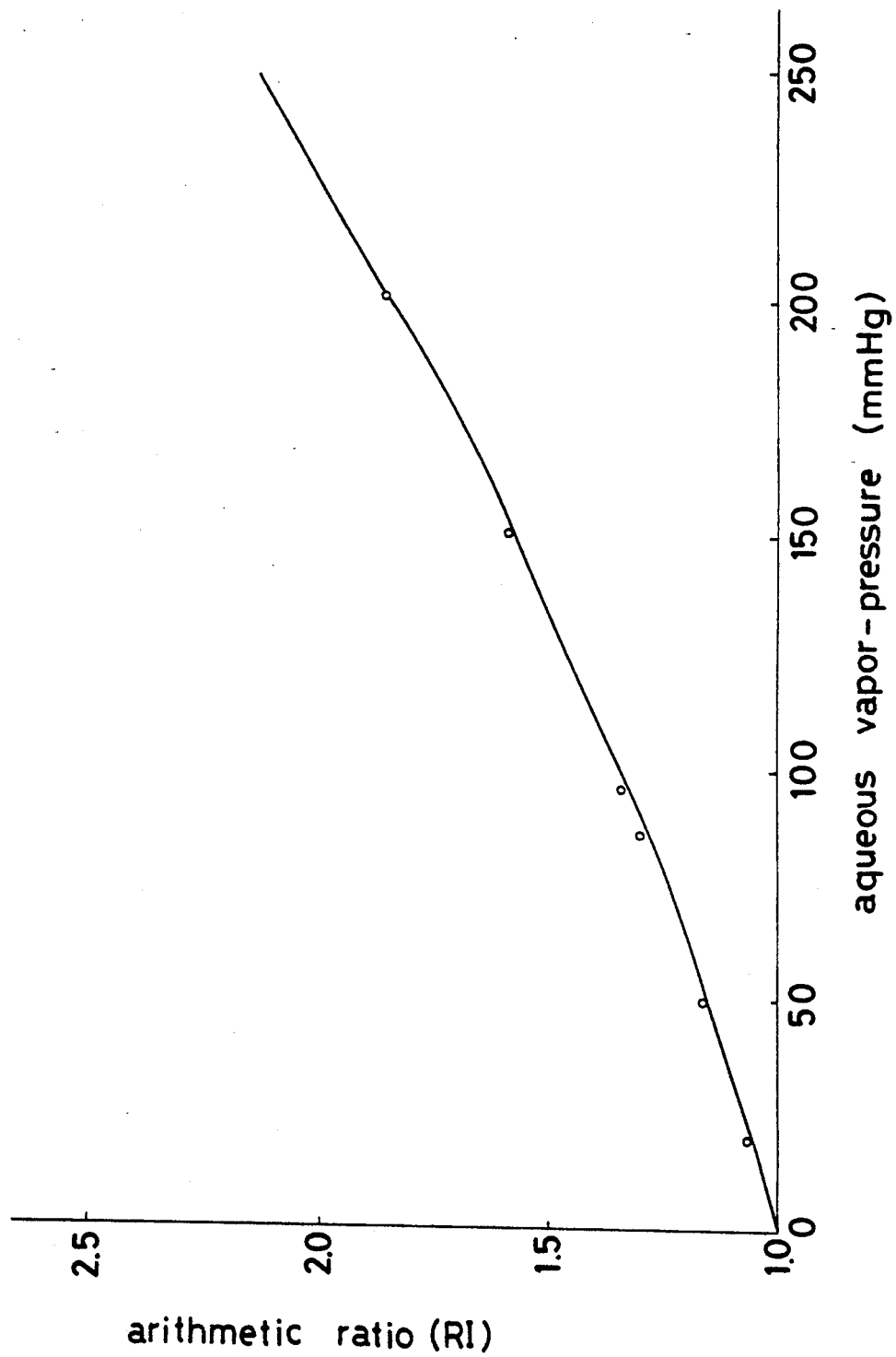
FIG. 7 is a view of a characteristic curve showing the relationship between an arithmetic ratio and aqueous vapor pressure.

On the other hand a relationship between the arithmetic ratio (RI) and aqueous vapor-pressure (mmHg) of the moisture-laden gas is given as shown in FIG. 7 which indicates that the arithmetic ratio (RI) is generally in proportion to the aqueous vapor-pressure (mmHg). When each voltage corresponding to the first flat portion (F1) and the second flat portion (F2) is applied by the voltage controller 101, while the diffusion limit current levels (IL1), (IL2) corresponding to the first flat portion (F1) and the second flat portion (F2) are determined by the current measurement portion 102, on the basis of the diffusion limit current levels (IL1), (IL2) the arithmetic ratio (RI) is given by the calculator portion 103, and the ratio (RI) is function of the aqueous vapor pressure which leads to the humidity of the gas. A relative humidity of the gas at a certain temperature is given by dividing the aqueous vapor pressure by a saturated aqueous vapor pressure of the same temperature.

As understood from the foregoing description, the invention is made on the basis of our discovery that the arithmetic ratio given by the first and second diffusion limit current remains substantially uniform under a certain humidity, and changes only depending on humidity of the gas regardless of the deterioration of the electrochemical cell when voltage is applied across the electrodes. In other word, the arithmetic ratio remains uniform and unchanged with lapse of time, etc., regardless of the solid electrolyte and the electrodes which are under the influence of the electrochemical cell which deteriorates with the passage of an operating period of time.

Since it is also found that the arithmetic ratio between the first and second diffusion limit current is substantially immune to the dimensional variation of the electrochemical cell, it enables to replace the sensor element so as to make it interchangeable when the sensor element was broken down.

The arithmetic ratio between the first and second diffusion limit current is calculated to readily ensure humidity of the moisture-laden gas, since the calculated ratio is in accordance with the humidity of the moisture-laden gas.

The characteristic curve between the arithmetic ratio and the aqueous vapor pressure of the gas to be measured is insured regardless of deterioration and dimensional variation from which the electrochemical cell sustains, thus enables to maintain measuring the humidity of the gas for an extended period of time at high accuracy. This is therefore electronically useful. Since the relation between the aqueous vapor pressure and the arithmetic ratio (RI) calculated by the analog circuit is on a constant and smooth curve as shown in FIG. 7, the humidity measurement of the gas can be easily done if the calculated (RI) is converted by a linearizing circuit to be an output of the vapor pressure. If a microcomputer is available, the relation between the vapor pressure and the ratio (RI) as shown in FIG. 7 can be put into an approximation equation or a direct table memory in advance thereby to quickly output the humidity level from the microcomputer only by feeding the arithmetic ratio of IL2/IL1.

Further, calculating the arithmetic ratio obviates the necessity of drying the moisture-laden gas and ensures the humidity measurement in good response with a relatively simple construction.

Figure 8:
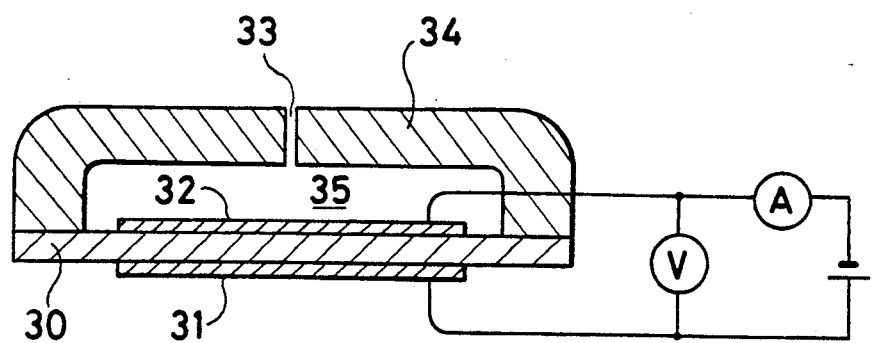
FIGS. 8 and 9 are cross sectional views of other types of electrochemical cells to which the present invention is applicable.
Figure 9:
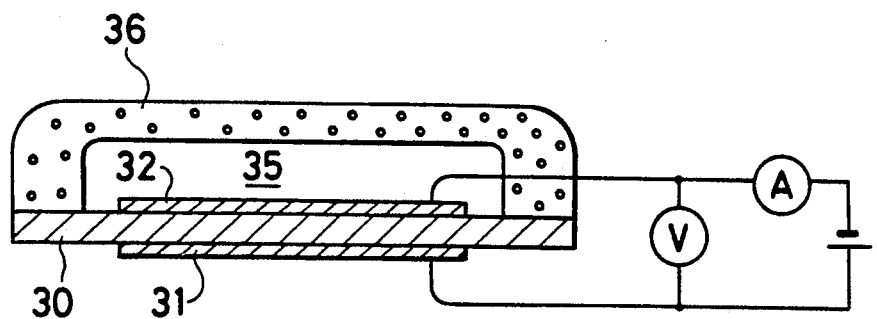

It is appreciated that electrodes 31, 32 may be placed in a manner to sandwich an oxygen-ion conductive plate 30 as shown in FIG. 8 wherein the cathode electrode 32 is covered by a coverlet 34 provided with a central throughhole 33. The central throughhole 33 works to effect a vapor diffusion limiting action and an oxygen gas diffusion limiting action towards a hollow space 35. In this instance, the cathode electrode 32 may be covered by a porous coverlet 36 to effect a moisture diffusion limiting action and an oxygen gas diffusion limiting action toward a hollow space 35 as shown in FIG. 9.

It is further noted that the arithmetic ratio (RI) between the first diffusion limit current (IL1) and second diffusion limit current (IL2) may be IL1/IL2 instead of IL2/IL1.

While the invention has been described with reference to the specific embodiments, it is understood that this description is not to be construed in a limiting sense as much as various modifications and additions to the specific embodiments may be made by skilled artisan without departing from the spirit and scope of the invention.

What is claimed is:

1. A method of measuring humidity by using an electrochemical cell which includes a solid oxygen-ion conductive electrolyte and a pair of electrodes tightly placed on a surface of the electrolyte, one of the electrodes being arranged to be exposed to moisture-laden gas so that an oxygen component of the gas is transferred from one electrode to the other electrode by a pumping action in accordance with an intensity of voltage applied across the pair of the electrodes;

the method of measuring humidity comprising the steps of:

applying the voltage across the pair of the electrodes to obtain a characteristic curve given by an intensity of the voltage and that of electrical current, the characteristic curve varying continuously from a first flat portion in which a first diffusion limit current generally remains constant within a first predetermined voltage range, passing through a point of an inflection with an increase of the applied voltage in which a second differential derivative of the characteristic curve falls to zero at a certain voltage, and ending up in a second flat portion in which a second diffusion limit current generally remains constant within a second predetermined voltage range;

reading out a value of the first diffusion limit current within the first predetermined voltage range;

reading out a value of the second diffusion limit current within the second predetermined voltage range; and calculating an arithmetic ratio given by the value of the first diffusion limit current and that of the second diffusion limit current so as to determine the humidity of the moisture-laden gas.

* * * * *